United States Patent
Bacus et al.

(10) Patent No.: US 8,512,967 B2
(45) Date of Patent: Aug. 20, 2013

(54) METHOD FOR PREDICTING THE RESPONSE TO HER2-DIRECTED THERAPY

(75) Inventors: Sarah S. Bacus, Hinsdale, IL (US); Bradley L. Smith, Marblehead, MA (US)

(73) Assignees: Ventana Medical Systems, Inc., Tucson, AZ (US); Cell Signaling Technology, Inc., Beverly, MA (US)

( * ) Notice: Subject to any disclaimer, the term of this patent is extended or adjusted under 35 U.S.C. 154(b) by 0 days.

(21) Appl. No.: 13/025,600

(22) Filed: Feb. 11, 2011

(65) Prior Publication Data

US 2011/0136149 A1 Jun. 9, 2011

Related U.S. Application Data

(60) Division of application No. 10/735,118, filed on Dec. 11, 2003, now abandoned, which is a continuation-in-part of application No. 10/408,520, filed on Apr. 7, 2003, now abandoned.

(60) Provisional application No. 60/432,942, filed on Dec. 11, 2002, provisional application No. 60/370,473, filed on Apr. 5, 2002.

(51) Int. Cl.
*G01N 33/574* (2006.01)

(52) U.S. Cl.
USPC .......................................................... 435/7.23

(58) Field of Classification Search
None
See application file for complete search history.

(56) References Cited

FOREIGN PATENT DOCUMENTS

EP 0656367 6/1995

OTHER PUBLICATIONS

Anderson et al (Int J Cancer, 2001, 94:774-782).*
Massarweh et al (Proc Am Soc Clinical Oncology, 2002, 21:abstract130).*
Tsang et al (Clinical Medicine Insights: Therapeutics, 2001:3; 1-13).*
Mueller et al (Int Journal Cancer, 2000, 89:384-388).*
Suo et al (Journal of Pathology, 2002, 196:17-25; published online Oct. 24, 2001).*
Gee et al (Int J Cancer, 2001, 95:247-254).*
Lane et al (Mol Cell Biology, 2000, 20:3210-3223).*
Slamon (European Journal of Oncology Nursing, 2000, 4:24-29).*
Albanell et al (Journal Clinical Oncology, Jan. 2002, 20:110-124).*
Bacus et al., "HER2/Neu Oncogene Expression and Proliferation in Breast Cancers," *American Journal of Pathology*, vol. 137, No. 1, pp. 103-111, 1990.
Bacus et al., "Differences in Response of Breast Cancer Molecular Profiles of Patients likely to Respond Either to erbB Tyrosine Kinase Inhibitors or to erbB Targeted Antibodies," *Breast Cancer Research and Treatment*, vol. 82, Suppl. 1, pp. S72-S73, 2003.
Guillernard et al., "Selective Delivery of Chemotherapeutics to Cancer Cells Via Growth Factor Receptors: Towards the Development of Smart Chemotherapeutic Agents," *Proceedings of the Annual Meeting of the American Association for Cancer Research*, pp. 76, 2002.
Köstler et al., "Insulin-like growth factor-1 receptor (IGF-1R) expression does not predict for resistance to trastuzumab-based treatment in patients with Her-2/neu overexpressing metastatic breast cancer," *Journal of Cancer Research and Clinical Oncology*, vol. 132, pp. 9-18, 2006.
Leitzel et al., "Increased Serum IGF Receptor (IGF-IR) in Patients With Elevated Serum HER-2/neu," *Breast Cancer Research and Treatment*, vol. 82, Suppl. 1, p. S94, 2003.
Lu et al., "Insulin-like growth factor-I receptor signaling and resistance to trastuzumab (Herceptin)," *Journal of the National Cancer Institute*, vol. 93, pp. 1852-1857, 2001.
Ruvinsky et al., "Ribosomal protein S6 phosphorylation: from protein synthesis to cell size," *Trends in Biochemical Sciences*, vol. 31, pp. 342-348, 2006.
Tockman et al., "Considerations in bringing a cancer biomarker to clinical application," *Cancer Research*, vol. 52, pp. 2711s-2718s, 1992.
iHOP, p. 1-2, printed Mar. 26, 2009.

* cited by examiner

*Primary Examiner* — Laura B Goddard
(74) *Attorney, Agent, or Firm* — Klarquist Sparkman, LLP

(57) ABSTRACT

This invention provides methods for determining or predicting response to HER2-directed therapy in an individual.

12 Claims, No Drawings

METHOD FOR PREDICTING THE RESPONSE TO HER2-DIRECTED THERAPY

CROSS REFERENCE TO RELATED APPLICATIONS

This is a divisional of U.S. patent application Ser. No. 10/735,118, filed Dec. 11, 2003, now abandoned; which is a continuation-in-part of U.S. patent application Ser. No. 10/408,520, filed Apr. 7, 2003, now abandoned; and claims the benefit of U.S. Provisional Application No. 60/370,473, filed Apr. 5, 2002, and U.S. Provisional Application No. 60/432,942, filed Dec. 11, 2002. Each of these applications is herein incorporated by reference.

BACKGROUND OF THE INVENTION

1. Field of the Invention

This invention relates to methods for predicting the response to HER2-directed therapy in an individual.

2. Background of the Invention

Cellular growth and differentiation processes involve growth factors that exert their actions through specific receptors expressed in the surfaces of responsive cells. Ligands binding to surface receptors, such as those that carry an intrinsic tyrosine kinase activity, trigger a cascade of events that eventually lead to cellular proliferation and differentiation (Carpenter et al., 1979, Biochem., 48: 193-216; Sachs et al., 1987, Cancer Res., 47: 1981-1986). Receptor tyrosine kinases can be classified into several groups on the basis of sequence similarity and distinct features. One of these groups includes the epidermal growth factor receptor family, which includes erbB-1 (also termed EGFR or HER-1) (Carpenter et al., supra); erbB-2 (HER-2/neu) (Semba et al., 1985, Proc. Natl. Acad. Sci., 82: 6497-6501; Coussens et al., 1985, Science, 230: 1130-1139; Bargmann et al., 1986, Cell, Vol. 45, 649-657); erbB-3 (HER-3) (Kraus et al., 1989, Proc. Natl. Acad. Sci., 86: 9193-9197; Carraway et al., 1994, J. Biol. Chem., 269: 14303-14306), and erbB-4 (HER-4) (Plowman et al., 1993, Nature, 366: 473-475; Tzahar et al., 1994, J. Biol. Chem., 269: 25226-25233).

Most tumors of epithelial origin express multiple erbB (HER) receptors and co-express one or more EGF-related ligands suggesting that autocrine-receptor activation plays a role in tumor cellular proliferation. Because these ligands activate different erbB/HER receptors, it is possible that multiple erbB receptor combinations might be active in a tumor, a characteristic that could influence its response to an erbB-targeted therapeutic. ErbB receptors form homodimers and heterodimers that can be stimulated by various ligands leading to downstream signaling events, the extent and nature of which depend on the combination of specific dimers and ligands. For example, HER2/neu appears to be the preferred heterodimerization partner with other members of the epidermal growth factor receptor family, but ultimately the dimers formed are determined by the ligand and the erbB receptors expressed in the cell. Not only may the ligand select the dimerization partners, but it may also influence the time course of membrane translocation, activation, and internalization of the receptor. For example, NDF/Heregulin can stimulate tyrosine phosphorylation of erbB-2 through heterodimerization with either receptors erbB-3 or erbB-4 (Peles et al., 1992, Cell 69, 205-216, Peles et al., 1993, EMBO J. 3, 961-71, Holmes et al., 1992, Science 256, 1205-1210; Tzahar et al., 1994, Biol. Chem., 269, 25226-25233; Plowman et al., 1993, Nature 366, 473-475; Pinkas-Kramarski et al., 1994, Proc. Natl. Acad. Sci. USA, 91, 9387-9391; Pinkas-Kramarski et al., 1996, J. Biol. Chem., 271, 19029-19032; Pinkas-Kramarski et al., 1998, Oncogene, 16, 1249-1258). Depending on the cell line studied, NDF/Heregulin can either elicit a growth arrest and differentiation phenotype, resulting in morphological changes, induction of lipids, and expression of intracellular adhesion molecule-1; or it can induce a mitogenic response (Holmes et al., 1992, Science, 256:1205-1210; Peles et al., 1992, Cell, 69:205-216; Bacus et al., 1993, Cancer Res. 53:5251-5261).

Downstream signaling after ligand binding may be determined by the set of docking proteins that may bind to the activated receptors. For example, activation of erbB receptor heterodimers is coupled to and stimulates downstream MAPK-Erk1/2 and PI3K-AKT growth and survival pathways, whose deregulation in cancer has been linked to disease progression and refractoriness to therapy (Tzahar et al., 1996, Mol. Cell. Biol. 16, 5276-5287; Fukazawa et al., 1996, J. Biol. Chem. 271, 14554-14559, Olayioye et al., 1998, Mol. Cell. Biol. 18, 5042-5051; Lange et al., 1998, J. Biol. Chem. 273, 31308-31316; Hackel et al., 1999, Curr. Opin. Cell Biol. 11, 184-189). HER-3 is a major docking site for phosphoinositide-3-kinase (PI3K). In addition, NDF/Heregulin stimulation causes activation of the PI3K pathway and phosphorylation of AKT (Altiok et al., 1999, J. Bio. Chem. 274, 32274-32278; Liu et al., 1999, Biochem. Biophys. Res. Comm. 261 897-903; Xing et al., 2000, Nature, Med. 6 189-195). These observations implicate PI3K/AKT in the signaling cascade that results from HER-3 heterodimerization with overexpressed HER-2/neu receptors in breast cancer cells; activation of PI3K/AKT promotes cell survival and enhanced tumor aggressiveness (Bacus et al., 2002, Oncogene 21, 3532-3540). In addition, AKT2 was reported to be activated and overexpressed in HER-2/neu-overexpressing breast cancers (Id.).

erbB-2/HER-2 is overexpressed in 20 to 30% of all breast cancers, and its overexpression is associated with poor prognosis, suggesting that it could be used as a target for antitumor agents (Slamon et al., 1987; Hudziak et al., 1989; Tagliabue et al., 1991). In erbB-2-overexpressing breast cancer cells, treatment with antibodies specific to HER-2/erbB-2 in combination with chemotherapeutic agents (such as cisplatin, doxorubicin, and taxol) elicits a higher cytotoxic response than treatment with chemotherapy alone (Hancock et al., 1991; Arteaga et al., 1994; Pietras et al., 1994). One possible mechanism by which HER-2/erbB-2 antibodies might enhance cytotoxicity to chemotherapeutic agents is through the modulation of the HER-2/erbB-2 protein expression (Bacus et al., 1992 & 1993; Stancovski et al., 1991; Klapper et al., 1997 & 2000), or by interfering with DNA repair (Arteaga et al., 1994 & 2001; Pietras et al., 1994).

Because of the effect of anti-HER-2/erbB-2 antibodies on cellular growth, a number of approaches have been used to therapeutically target HER-2/erbB-2- or EGFR-overexpressing cancers. For clinical use, one approach is to interfere with the kinase activity of the receptor by using inhibitors that block the nucleotide binding site of HER-2/neu or EGFR (Bruns et al., 2000; Christensen et al, 2001, Erlichman et al., 2001, Herbst et al., 2002; Hidalgo et al, 2001; Moasser et al, 2001; Fujimura et al., 2002; Normanno et al., 2002). A second approach is using ansamycins to influence the stability of HER2/neu receptors (Munster et al., 2002; Basso et al, 2002). Another approach is the use of antibodies directed to various erbB receptors, specifically EGFR or HER-2/neu (Alaoui-Jamali et al., 1997; Albanell et al., 2001(a); Baselga et al., 1994 & 2002; Mendelsohn, 1990). Analysis of various antibodies to HER-2/neu led to the identification of the murine monoclonal, 4D5. This antibody recognizes an extracellular epitope (amino acids 529 to 627) in the cysteine-rich II domain that resides very close to the transmembrane region. Treatment of breast cancer cells with 4D5 partially blocks NDF/heregulin activation of HER-2-HER-3 complexes, as measured by receptor phosphorylation assays. To allow for chronic human administration, murine 4D5 was fully humanized to generate trastuzumab/HERCEPTIN® (Sliwkowski et al., 1999; Ye et al., 1999; Carter et al, 1992; Fujimoto-Ouchi et al, 2002; Vogel, et al., 2001 & 2002).

A number of monoclonal antibodies and small molecule, tyrosine kinase inhibitors targeting EGFR or erbB-2 have been developed. For example, HERCEPTIN® is approved for treating the 25% of women whose breast cancers overexpress erbB-2 protein or demonstrate erbB-2 gene amplification (Cobleigh et al., 1999, *J. Clin. Oncol.* 17, 2639-2648). In addition, several EGFR-targeted therapies are currently under clinical investigation (Mendelsohn & Baselga, 2000, *Oncogene* 19, 6550-6565; Xia et al., 2002, *Oncogene* 21, 6255-6263).

The development of successful oncological drugs has followed a well-established evaluation process including phases I, II, and III clinical trial. Phase I studies aim to determine the maximally tolerated dose of the drug, its optimal schedule of administration and the dose-limiting toxicities. Historically, cytotoxic cancer therapies have been developed based on maximum tolerated doses (MTD), treating patients without understanding the tumor profile for likely responders. Hence, patients were often subjected to toxic therapies with limited therapeutic benefit. Recently, elucidating tumor growth and survival pathways has led to the development of tumor-targeted therapies. For such targeted therapeutics that are not expected to produce serious adverse side effects, relying on a MTD may not be suitable. More relevant may be the determination of the optimal dose and schedule that is sufficient to inhibit cellular signaling in patient samples. Biological assays for signaling biomarkers are needed to establish such a protocol.

Preclinically, most erbB-receptor targeted therapies primarily exert cytostatic anti-tumor effects, necessitating their chronic administration in clinical practice. Identification of biologically effective doses (BED), the dose or dose range that maximally inhibits the intended target, beyond which dose escalation is likely to add toxicity without benefit, is therefore essential. Moreover, many of these agents will be used in combination with cytotoxic therapies, where added toxicity may not be tolerable, further supporting BED-based dosing. "Targeted-therapy" implies that populations of likely responders exists, and can be identified.

In view of the severe and deleterious consequences of administering an inappropriate or ineffective therapy to a human cancer patient, there exists a need in the art for predicting the response to cancer therapy in an individual. Further, there is a need to develop diagnostics that are capable of predicting patient response for the successful development and clinical acceptance of new HER-2 targeted therapeutics similar to HERCEPTIN®.

SUMMARY OF THE INVENTION

This invention provides methods for predicting a response of an individual to a HER2-directed therapy.

In a first aspect, the invention provides methods for identifying a mammalian tumor that responds to a HER2-directed therapy, wherein the mammalian tumor overexpresses HER2, the method comprising the step of assaying a sample obtained from the mammalian tumor to detect a pattern of expression, phosphorylation or both expression and phosphorylation of one or a plurality of polypeptides consisting of:
  (a) IGFR polypeptide;
  (b) EGFR polypeptide;
  (c) NDF polypeptide;
  (d) phosphorylated S6 ribosomal polypeptide;
  (e) phosphorylated AKT polypeptide; and
  (f) phosphorylated ERK polypeptide;
wherein the particular combination of polypeptides and pattern of expression, phosphorylation or both expression and phosphorylation identifies mammalian tumors that respond to a HER2-directed therapy.

In certain embodiments, the pattern that identifies a mammalian tumor as responding is decreased expression of IGFR polypeptide in the mammalian tumor as compared to a non-tumor tissue or cell sample. In other embodiments, the detected pattern is normal or increased expression of IGFR polypeptide, accompanied by decreased phosphorylation of AKT polypeptide, decreased phosphorylation of S6 ribosomal polypeptide or both in the mammalian tumor as compared to a non-tumor tissue or cell sample. In further embodiments, the detected pattern is normal or increased expression of EGFR polypeptide, accompanied by decreased phosphorylation of ERK polypeptide in the mammalian tumor as compared to a non-tumor tissue or cell sample. In additional embodiments, the detected pattern is decreased expression of IGFR polypeptide, accompanied by increased phosphorylation of S6 ribosomal polypeptide in the mammalian tumor as compared to a non-tumor tissue or cell sample. In other embodiments, the detected pattern is decreased expression of IGFR polypeptide, accompanied by increased expression of NDF polypeptide in the mammalian tumor as compared to a non-tumor tissue or cell sample; where further the detected pattern can include increased phosphorylation of S6 ribosomal polypeptide.

In a second aspect, the invention provides methods for identifying a mammalian tumor that does not respond to a HER2-directed therapy, wherein the mammalian tumor overexpresses HER2, the method comprising the step of assaying a sample obtained from the mammalian tumor to detect a pattern of expression, phosphorylation or both expression and phosphorylation of one or a plurality of polypeptides consisting of:
  (a) IGFR polypeptide;
  (b) EGFR polypeptide;
  (c) NDF polypeptide;
  (d) phosphorylated S6 ribosomal polypeptide;
  (e) phosphorylated AKT polypeptide; and
  (f) phosphorylated ERK polypeptide;
wherein the particular combination of polypeptides and pattern of expression, phosphorylation or both expression and phosphorylation identifies mammalian tumors that do not respond to a HER2-directed therapy.

In certain embodiments, the pattern that identifies a mammalian tumor as not responding is normal or increased expression of IGFR polypeptide, accompanied by increased phosphorylation of AKT polypeptide, increased phosphorylation of S6 ribosomal polypeptide, or both in the mammalian tumor as compared to a non-tumor tissue or cell sample. In other embodiments, the detected pattern is decreased expression of EGFR polypeptide and increased expression of NDF polypeptide in the mammalian tumor as compared to a non-tumor tissue or cell sample. In further embodiments, the detected pattern is decreased expression of EGFR polypeptide in the mammalian tumor as compared to a non-tumor tissue or cell sample. In other embodiments, the detected pattern is decreased expression of NDF polypeptide in the mammalian tumor as compared to a non-tumor tissue or cell sample. In additional embodiments, the detected pattern is decreased expression of EGFR polypeptide and increased phosphorylation of ERK polypeptide in the mammalian tumor as compared to a non-tumor tissue or cell sample. In further embodiments, the detected pattern is normal or increased expression of IGFR polypeptide and decreased expression of NDF in the mammalian tumor as compared to a non-tumor tissue or cell sample.

In a third aspect, the invention provides methods of selecting a subject with cancer for treatment with a molecule targeting HER2, wherein the cancer overexpresses HER2, the methods comprising the steps of:
(a) determining the pattern of expression, phosphorylation or both expression and phosphorylation in a cell or tissue sample from the subject of one or a plurality of polypeptides consisting of:
 (i) IGFR polypeptide;
 (ii) EGFR polypeptide;
 (iii) NDF polypeptide;
 (iv) phosphorylated S6 ribosomal polypeptide;
 (v) phosphorylated AKT polypeptide; and
 (vi) phosphorylated ERK polypeptide; and
(b) selecting the subject based on the detected pattern of expression, phosphorylation, or both expression and phosphorylation. The particular combination of polypeptides and pattern of expression, phosphorylation or both expression and phosphorylation is used to select the subjects with cancer for treatment with a molecule targeting HER2.

In certain embodiments, the detected pattern for selecting a subject for treatment with a molecule targeting HER2 is decreased expression of IGFR polypeptide in the mammalian tumor as compared to a non-tumor tissue or cell sample. In other embodiments, the detected pattern is normal or increased expression of IGFR polypeptide, accompanied by decreased phosphorylation of AKT polypeptide, decreased phosphorylation of S6 ribosomal polypeptide or both in the mammalian tumor as compared to a non-tumor tissue or cell sample. In further embodiments, the detected pattern is normal or increased expression of EGFR polypeptide, accompanied by decreased phosphorylation of ERK polypeptide in the mammalian tumor as compared to a non-tumor tissue or cell sample. In additional embodiments, the detected pattern is decreased expression of IGFR polypeptide, accompanied by increased phosphorylation of S6 ribosomal polypeptide in the mammalian tumor as compared to a non-tumor tissue or cell sample. In other embodiments, the detected pattern is decreased expression of IGFR polypeptide, accompanied by increased expression of NDF polypeptide in the mammalian tumor as compared to a non-tumor tissue or cell sample; where further the detected pattern can include increased phosphorylation of S6 ribosomal polypeptide.

In a fourth aspect, the invention provides methods of selecting a subject with cancer to not receive treatment with a molecule targeting HER2, wherein the cancer overexpresses HER2, the methods comprising the steps of:
(a) determining the pattern of expression, phosphorylation or both expression and phosphorylation in a cell or tissue sample from the subject of one or a plurality of polypeptides consisting of:
 (i) IGFR polypeptide;
 (ii) EGFR polypeptide;
 (iii) NDF polypeptide;
 (iv) phosphorylated S6 ribosomal polypeptide;
 (v) phosphorylated AKT polypeptide; and
 (vi) phosphorylated ERK polypeptide; and
(b) selecting the subject based on the detected pattern of expression, phosphorylation, or both expression and phosphorylation. The particular combination of polypeptides and pattern of expression, phosphorylation or both expression and phosphorylation is used to select the subjects with cancer to not receive treatment with a molecule targeting HER2.

In certain embodiments, the detected pattern for selecting a subject not to receive treatment with a molecule targeting HER2 is normal or increased expression of IGFR polypeptide, accompanied by increased phosphorylation of AKT polypeptide, increased phosphorylation of S6 ribosomal polypeptide, or both in the mammalian tumor as compared to a non-tumor tissue or cell sample. In other embodiments, the detected pattern is decreased expression of EGFR polypeptide and increased expression of NDF polypeptide in the mammalian tumor as compared to a non-tumor tissue or cell sample. In further embodiments, the detected pattern is decreased expression of EGFR polypeptide in the mammalian tumor as compared to a non-tumor tissue or cell sample. In other embodiments, the detected pattern is decreased expression of NDF polypeptide in the mammalian tumor as compared to a non-tumor tissue or cell sample. In additional embodiments, the detected pattern is decreased expression of EGFR polypeptide and increased phosphorylation of ERK polypeptide in the mammalian tumor as compared to a non-tumor tissue or cell sample. In further embodiments, the detected pattern is normal or increased expression of IGFR polypeptide and decreased expression of NDF in the mammalian tumor as compared to a non-tumor tissue or cell sample.

In various aspects of the invention, including those mentioned above, the detection of phosphorylation of AKT polypeptide, phosphorylation of S6 ribosomal polypeptide, or both can determined subsequent to contacting the sample obtained from the mammalian tumor with a HER2-directed therapy. Further, the HER2-directed therapy can be or comprise rhuMAb HER2 (HERCEPTIN®). In addition, the sample can be contacted with at least one chemotherapeutic agent. Further, the detected pattern of expression, phosphorylation, or both, of one or a plurality of polypeptides (a) through (f) can be determined using a biodetection reagent. The biodetection reagent can be an antibody or a nucleic acid probe. Further, the detected pattern of phosphorylated AKT polypeptide can be determined using an antibody specific for an epitope comprising a phosphorylated serine residue at position 473, the detected pattern of phosphorylated S6 ribosomal polypeptide can be determined using an antibody specific for an epitope comprising a phosphorylated serine residue at position 235, and/or the detected pattern of phosphorylated ERK polypeptide can be determined using an antibody specific for an epitope comprising a phosphorylated threonine residue at position 202 and a phosphorylated tyrosine residue at position 204. Further, the sample obtained from the mammalian tumor can be a paraffin-embedded biopsy sample. Also, the mammalian tumor can be identified as overexpressing HER2 using an antibody that binds HER2 polypeptide.

In a fifth embodiment, the invention provides kits for characterizing a mammalian tumor's responsiveness to a HER2-directed therapy, the kit comprising:
(a) an antibody that binds IGFR polypeptide,
and one or more of the following:
(b) an antibody that binds phosphorylated AKT polypeptide;
(c) an antibody that binds phosphorylated S6 ribosomal polypeptide;
(d) an antibody that binds EGFR polypeptide;

(e) an antibody that binds HER2 polypeptide;
(f) an antibody that binds NDF polypeptide; and
(g) an antibody that binds phosphorylated ERK polypeptide.

In certain embodiments, the antibody of (b) is immunologically specific for AKT polypeptide having a phosphorylated serine residue at position 473; antibody of (c) is immunologically specific for S6 ribosomal polypeptide having a phosphorylated serine residue at position 235; and/or the antibody of (f) is immunologically specific for EKT polypeptide having a phosphorylated threonine residue at position 202 and a phosphorylated tyrosine at position 204. In other embodiments, the kit further comprises at least one secondary antibody that binds to an antibody of subpart (a) through (g).

Specific embodiments of the present invention will become evident from the following more detailed description of certain preferred embodiments and the claims.

Sequence Listing

The Sequence Listing is submitted as an ASCII text file in the form of the file named Sequence_Listing.txt, which was created on Feb. 10, 2011, and is 10,043 bytes, which is incorporated by reference herein.

DETAILED DESCRIPTION OF THE PREFERRED EMBODIMENTS

This invention provides methods for predicting response in cancer subjects to cancer therapy, including human cancer patients. In addition, this invention provides predictive biomarkers to identify the cancer patients for whom the administering a therapeutic agent will be most effective, including a therapeutic agent for treating breast cancer. Specifically, this invention provides predictive biomarkers for assessing the efficacy of therapeutic agents targeted to Her2/neu, including such agents such as HERCEPTIN®.

In contrast to traditional anticancer methods, where chemotherapeutic drug treatment is undertaken as an adjunct to and after surgical intervention, neoadjuvant (or primary) chemotherapy consists of administering drugs as an initial treatment in certain cancer patients. One advantage of such an approach is that, for primary tumors of more than 3 cm, it permits the later or concomitant use of conservative surgical procedures (as opposed to, e.g., radical mastectomy in breast cancer patients) for the majority of patients, due to the tumor shrinking effect of the chemotherapy. Another advantage is that for many cancers, a partial and/or complete response is achieved in about two-thirds of all patients. Finally, because the majority of patients are responsive after two to three cycles of chemotherapeutic treatment, it is possible to monitor the in vivo efficacy of the chemotherapeutic regimen employed, in order to identify patients whose tumors are non-responsive to chemotherapeutic treatment. Timely identification of non-responsive tumors allows the clinician to limit a cancer patient's exposure to unnecessary side-effects of treatment and to institute alternative treatments. Unfortunately, methods present in the art, including histological examination, are insufficient for such a timely and accurate identification. The present invention provides methods for developing more informed and effective regimes of therapy that can be administered to cancer patients with an increased likelihood of an effective outcome (i.e., reduction or elimination of the tumor).

A cancer diagnosis, both an initial diagnosis of disease and subsequent monitoring of the disease course (before, during, or after treatment) is conventionally confirmed through histological examination of cell or tissue samples removed from a patient. Clinical pathologists need to be able to accurately determine whether such samples are benign or malignant and to classify the aggressiveness of tumor samples deemed to be malignant, because these determinations often form the basis for selecting a suitable course of patient treatment. Similarly, the pathologist needs to be able to detect the extent to which a cancer has grown or gone into remission, particularly as a result of or consequent to treatment, most particularly treatment with chemotherapeutic or biological agents.

Histological examination traditionally entails tissue-staining procedures that permit morphological features of a sample to be readily observed under a light microscope. A pathologist, after examining the stained sample, typically makes a qualitative determination of whether the tumor sample is malignant. It is difficult, however, to ascertain a tumor's aggressiveness merely through histological examination of the sample, because a tumor's aggressiveness is often a result of the biochemistry of the cells within the tumor, such as protein expression or suppression and protein phosphorylation, which may or may not be reflected by the morphology of the sample. Therefore, it is important to be able to assess the biochemistry of the cells within a tumor sample. Further, it is desirable to be able to observe and quantitate both gene expression and protein phosphorylation of tumor-related genes or proteins, or more specifically cellular components of tumor-related signaling pathways.

Cancer therapy can be based on molecular profiling of tumors rather than simply their histology or site of the disease. Elucidating the biological effects of targeted therapies in tumor tissue and correlating these effects with clinical response helps identify the predominant growth and survival pathways operative in tumors, thereby establishing a pattern of likely responders and conversely providing a rational for designing strategies to overcome resistance. Successful diagnostic targeting of a growth factor receptor must determine if tumor growth or survival is being driven by the targeted receptor or receptor family, by other receptors not targeted by the therapy, and whether downstream signaling suggests that another oncogenic pathway is involved.

For subjects considered for treatment with HERCEPTIN®, it is necessary to consider additional biomarkers beyond the presence of the target HER-2/neu, at least because the status of the EGFR and erbB ligands NDF and TGF-α affect HERCEPTIN® therapy response in breast cancer patients. Therefore, considering HER2/neu expression alone does not necessarily predict overall erbB oncogenic activity or potential response to erbB inhibitors. In addition, previous studies have shown that not all tumor cells respond to inhibition of ErbB receptors, despite exhibiting aberrant EGFR and/or HER2/neu expression. Examples include the MKN7 and BT474 erbB receptor-overexpressing carcinoma cell lines: BT474 cells respond to HERCEPTIN® but MKN7 cells do not (Motoyama, et al., *Cancer Research*, 62, 3151-3158 (2002)). In addition, the proliferation block induced as a consequence of decreased EGFR or HER2 receptor activity, such as by the activity of an erbB-inhibitor, may be overcome by the presence of EGF-related ligands such as EGF or NDF/Heregulin (Id). This phenomenon can be attenuated using a bispecific ErbB-1/ErbB-2 inhibitor, thus supporting increased antitumor efficacy through simultaneous inhibition of multiple ErbB receptors.

In addition, in many cancers NDF/Heregulin or TGF-α expression produces an autocrine loop of HER-2/EGFR heterodimerization. Downregulation of HER-2/neu expression is an important way of inhibiting signals generated by these heterodimers. Downregulation can be accomplished by treatment with HERCEPTIN®, which produces receptor endocytosis. Furthermore, high levels of phosphorylated ERK (or pAKT) can be a negative predictor for positive treatment outcome, when observed in conjunction with the expression of EGFR and the presence of NDF, suggesting the existence of other pathways that might promote proliferation of the tumor cellular growth. High pERK is also associated with resistance to HERCEPTIN® through downregulation of p27; this may implicate other signals (such as estrogen receptor's cross activation of the MAPK and AKT pathways) that may contribute to high pERK and thus contribute to proliferation of the tumor cells growth. In addition, phosphorylated AKT has been shown to be an important part of the response to HERCEPTIN®, as high pAKT-positive patients had poor response to HERCEPTIN®. High-phosphorylated AKT has been shown to be associated with high expression of insulin like growth factor receptors (IGFR-1) as well as PDGFR and results in resistance to HERCEPTIN®. Interestingly, data from clinical trials have shown that using a dual inhibitor (i.e., specific for HER-1/neu and HER-2/neu) has clinical efficacy in patients when treatment induced downregulation of pERK and pAKT, but not in patients in which pERK and pAKT levels didn't diminish after treatment. Thus, in those patients who overexpressed HER-1 and HER-2, as well as pERK and pAKT, antitumor activity was dependent on HER-1 and HER-2 receptor activation and a clinical response was observed. In contrast, in patients for whom pERK and pAKT activity remained high after treatment with a dual inhibitor, clinical response didn't occur. Combination therapies can have clinical significance. A combination of the ErbB-1-directed monoclonal antibodies mAb 225 and mAb 4D5 inhibited proliferation of an ovarian tumor cell line more strongly than either mAb alone (Ye et al., 1999, *Oncogene* 18: 731-8). In addition to ErbB-targeted mAbs, a number of different ErbB-1/ErbB-2-bispecific inhibitors, also referred to as dual EGFR/erbB-2 kinase inhibitors, have been described recently, such as GW572016 and PKI166, that are currently in clinical trials (Motoyama et al., 2002, *Cancer Research* 62: 3151-3158). Therefore, response to HERCEPTIN® is affected by the expression of multiple erbB receptors and their ligands in tumors.

Thus, HER-2/neu overexpression alone is not the only predictor of response to molecules such as HERCEPTIN®. HER-2/neu is an orphan, ligandless receptor in need of its partners EGFR (HER-1) and HER-3 in order to exert its activity. HER-1 and HER-3 heterodimerization with HER-2 is enhanced by the presence of EGF or NDF (Tzahar et al., 1996, *EMBO J.* 15: 254-64, Graus-Porta, 1997, *EMBO J.*, 16 1647-55), and thus HER-2 activity is dependent on HER-1 or HER-3. Other receptors may also transactivate the erbB receptors. These receptors may be mediating tumorigenesis through signaling to downstream proliferative and survival pathways. For example, the IGFR receptor may mediate patient response to breast cancer therapies targeting HER2/neu. High IGFR expression combined with high S6 ribosomal protein phosphorylation correlates with poor patient response regardless of erb-B expression, indicating that IGFR acts directly to activate signaling downstream of erb-B receptors rather than through transactivation of erb-B receptors. Cell line studies also have suggested a role for IGFR in patient response. HERCEPTIN® resistance has been suggested to occur though activation of IGFR (Lu et al., 2001, *J. National Cancer Institute* 93: 1852). In addition, co-targeting IGFR as well as HER2/neu has been shown to produce synergistic inhibition of growth in breast cancer cells (Camirand et al., 2002, *Med Sci Monit.* 8: (12): BR521-6). Therefore, analysis of IGFR expression and downstream signaling can be critical for an accurate assessment of potential HERCEPTIN® response in breast cancer patients.

Thus, there is no one marker of downstream signaling protein activation that would integrate multiple upstream signals and predict response. However, analysis of p-ERK and p-AKT has been found to be predictive in patients overexpressing EGFR. Therefore, in the presence of active erbB receptors, high ERK and AKT signaling indicates that HERCEPTIN® therapy is less likely to be effective. AKT activation has been shown to result in HERCEPTIN® resistance in breast cancer cell lines (Yakes, et al., 2002, *Cancer Res.* 62: 4132-41; Clark et al., 2202, *Mol. Cancer Ther.* 1: 707-17). In addition, analysis of S6 ribosomal protein phosphorylation greatly increased the predictive power of IGFR expression. In patients with high S6 phosphorylation, positive response ranged from 8% to 67% based upon IGFR expression. Approximately 30% of patients with low S6 phosphorylation responded, regardless of IGFR expression. These results were also reflected in an analysis of clinical samples, in which only those patients that lacked active IGFR signaling responded to HERCEPTIN® therapy. IGF signaling in breast cancer occurs through AKT activation (Oh et al., 2002, *Neoplasia* 4: 204-17; Dufourny et al., 1997, *J Biol Chem.* 272: 31163-71), which leads to S6 ribosomal protein phosphorylation. Hence, S6 phosphorylation can be indicative of active IGF signaling in those tumors over-expressing IGFR.

Analysis of down-stream signaling and patient response is complicated when chemotherapy and radiotherapy therapy is included in addition to HERCEPTIN® treatment. AKT and MAP kinase pathway activation, for example, are known to play a role in response to DNA-damaging agents (Clark et al., 2002, *Mol. Cancer Ther.* 1: 707-17; Bacus et al., 2001, *Oncogene* 20: 147-155). Consideration of downstream signaling in patients undergoing a combination of therapies provides additional predictive information not obtained solely from analysis of receptor or ligand expression levels. Analysis of patients treated with HERCEPTIN® as a single agent therapy can be used to determine which of the identified biomarkers mediated the response to Herceptin,® as opposed to the biomarkers that mediate the response to the other therapies. Nonetheless, the identified biomarkers are useful, among other things, for designing diagnostics for breast cancer patients undergoing the common HERCEPTIN® combination therapies.

Further, up-regulation of the AKT/mTOR pathway by Heregulin/NDF is an important predictor for response. pAKT has been associated with high levels of Cyclin E and low levels of the cyclin inhibitor p27.

Before administration of HER2-targeted therapies, a panel of diagnostics of each tumor is used according to the methods of this invention to find the best candidate for each therapy. According to the methods of this invention, treatment by a HER2-targeted therapy, such as HERCEPTIN®, is effective when a patient's tumor growth depends on a cellular pathway such as AKT/mTOR that is driven by the erbB receptors and not by other tyrosine kinases, such as Insulin-like Growth Factor Receptors (IGFR). When high levels of activation of these downstream signals occur independent of erbB receptors, HERCEPTIN® treatment is not effective. Use of the methods of this invention permits a clinician to choose a more effective combination of targeted therapies for cancer patients.

The HER2-directed therapies of the present invention can include, for example, rhuMAb HER2, otherwise known as HERCEPTIN®. The samples obtained from the mammalian tumor can be contacted with at least one chemotherapeutic agent, for example cisplatin, doxorubicin, or taxol.

Automated (computer-aided) image analysis systems known in the art can augment visual examination of tumor samples. In a representative embodiment, the cell or tissue sample is exposed to detectably-labeled reagents specific for a particular biological marker, and the magnified image of the cell is then processed by a computer that receives the image from a charge-coupled device (CCD) or camera such as a television camera. Such a system can be used, for example, to detect and measure expression and activation levels of EGFR, HER2, HER3, pERK, NDF, TGF-α, IGFR, pS6, and pAKT in a sample, or any additional diagnostic biomarkers. Thus, the methods of the invention provide more accurate cancer diagnosis and better characterization of gene expression in histologically identified cancer cells, most particularly with regard to expression of tumor marker genes or genes known to be expressed in particular cancer types and subtypes (e.g., having different degrees of malignancy). This information permits a more informed and effective regimen of therapy to be administered, because drugs with clinical efficacy for certain tumor types or subtypes can be administered to patients whose cells are so identified.

Another drawback of conventional anticancer therapies is that the efficacy of specific chemotherapeutic agents in treating a particular cancer in an individual human patient is unpredictable. In view of this unpredictability, the art is unable to determine, prior to starting therapy, whether one or more selected agents would be active as anti-tumor agents or to render an accurate prognosis of course of treatment in an individual patient. This is especially important because a particular clinical cancer may present the clinician with a choice of treatment regimens, without any current way of assessing which regimen will be most efficacious for a particular individual. It is an advantage of the methods of this invention that they are able to better assess the expected efficacy of a proposed therapeutic agent (or combination of agents) in an individual patient. The claimed methods are advantageous for the additional reasons that they are both time- and cost-effective in assessing the efficacy of chemotherapeutic regimens and are minimally traumatic to cancer patients.

Methods of this invention can be used to identify a mammalian tumor that responds to HER-2 directed therapies. Further, methods of this invention can be used to select a subject with cancer for treatment with a molecule targeting HER. Moreover, methods of this invention can be used to identify a mammalian tumor that does not respond to HER-2 directed therapies. Further, methods of this invention can be used to select a subject with cancer to not receive treatment with a molecule targeting HER2.

Patterns of expression and phosphorylation of polypeptides are detected and quantified using methods of the present invention. More particularly, patterns of expression and phosphorylation of polypeptides that are cellular components of a tumor-related signaling pathway are detected and quantified using methods of the present invention. For example, the patterns of expression and phosphorylation of polypeptides can be detected using biodetection reagents specific for the polypeptides. For example, the biodetection reagents can be antibodies. Alternatively, the biodetection reagents can be nucleic acid probes. A nucleic acid probe is defined to be a collection of one or more nucleic acid fragments whose hybridization to a sample can be detected. The probe may be unlabeled or labeled so that its binding to the target or sample can be detected. The probe is produced from a source of nucleic acids from one or more particular (preselected) portions of the genome, e.g., one or more clones, an isolated whole chromosome or chromosome fragment, or a collection of polymerase chain reaction (PCR) amplification products. The nucleic acid probe may also be isolated nucleic acids immobilized on a solid surface (e.g., nitrocellulose, glass, quartz, fused silica slides), as in an array. The probe may be a member of an array of nucleic acids as described, for instance, in WO 96/17958. Techniques capable of producing high density arrays can also be used for this purpose (see, e.g., Fodor (1991) Science 767-773; Johnston (1998) Cum Biol. 8: R171-R174; Schummer (1997) Biotechniques 23: 1087-1092; Kern (1997) Biotechniques 23: 120-124; U.S. Pat. No. 5,143,854). One of skill will recognize that the precise sequence of the particular probes can be modified to a certain degree to produce probes that are "substantially identical," but retain the ability to specifically bind to (i.e., hybridize specifically to) the same targets or samples as the probe from which they were derived. The term "nucleic acid" refers to a deoxyribonucleotide or ribonucleotide in either single- or double-stranded form. The term encompasses nucleic acids, i.e., oligonucleotides, containing known analogues of natural nucleotides that have similar or improved binding properties, for the purposes desired, as the reference nucleic acid. The term also includes nucleic acids which are metabolized in a manner similar to naturally occurring nucleotides or at rates that are improved for the purposes desired. The term also encompasses nucleic-acid-like structures with synthetic backbones. One of skill in the art would recognize how to use a nucleic acid probes for screening of cancer cells in a sample by reference, for example, to U.S. Pat. No. 6,326,148, directed to screening of colon carcinoma cells.

Polypeptides associated with breast cancer can be quantified by image analysis using a suitable primary antibody against biomarkers, including but not limited to EGFR, HER-2, HER-3, IGFR, NDF, TGF-α, p-ERK, pS6, or p-AKT, detected directly or using an appropriate secondary antibody (such as rabbit anti-mouse IgG when using mouse primary antibodies) and/or a tertiary avidin (or Strepavidin) biotin complex ("ABC").

Examples of reagents useful in the practice of the methods of the invention as exemplified herein include antibodies specific for HER2/neu, including but not limited to the mouse monoclonal antibody CB11, obtained from Ventana Medical Systems, Inc. (VMSI, Tucson, Ariz.). In addition, reagents useful in the practice of the methods of the invention include antibodies specific for phosphorylated AKT, including but not limited to antibodies specific for a phosphorylated serine residue of position 473, wherein the sequence of AKT is represented by SEQ ID NO:1 (Table 8). Further, reagents useful in the practice of the methods of the invention include antibodies specific for phosphorylated S6, including but not limited to antibodies specific for a phosphorylated serine residue of position 235, wherein the sequence of S6 is represented by SEQ ID NO:2 (Table 8). Also, reagents useful in the practice of the methods of the invention include antibodies specific for phosphorylated ERK, including but not limited to antibodies specific for a phosphorylated threonine residue at position 202 and a phosphorylated tyrosine residue of position 204, wherein the sequence of ERK is represented by SEQ ID NO:3 (Table 8).

Further, the pattern of expression, phosphorylation, or both expression and phosphorylation of the predictive polypeptides can be compared to a non-tumor tissue or cell sample. The non-tumor tissue or cell sample can be obtained from a non-tumor tissue or cell sample from the same individual, or alternatively, a non-tumor tissue or cell sample from a different individual. A detected pattern for a polypeptide is referred to as decreased in the mammalian tumor, tissue, or cell sample, if there is less polypeptide detected as compared to the a non-tumor tissue or cell sample. A detected pattern for a polypeptide is referred to as increased in the mammalian tumor, tissue, or cell sample, if there is more polypeptide detected as compared to the a non-tumor tissue or cell sample. A detected pattern for a polypeptide is referred to as normal in the mammalian tumor, tissue, or cell sample, if there is the same, or approximately the same, polypeptide detected as compared to the a non-tumor tissue or cell sample.

The methods of this invention for identifying mammalian tumors that respond, or that do not respond, to a HER2-directed therapy comprise the step of assaying a sample obtained from the mammalian tumor to detect a pattern of expression, phosphorylation or both of one or a plurality of polypeptides consisting of: (a) IGFR polypeptide; (b) EGFR polypeptide; (c) NDF polypeptide; (d) phosphorylated S6 ribosomal polypeptide; (e) phosphorylated AKT polypeptide; (f) phosphorylated EKT polypeptide. The combination of polypeptides and pattern of expression, phosphorylation, or both expression and phosphorylation identifies mammalian tumors that respond, or that do not respond, to a HER2-directed therapy. The methods can include the detection of a pattern of expression, phosphorylation or both of one, two, three, four, five, or all six of these polypeptides. Further, the methods can, but need not, include other steps, including steps such as the detection of a pattern of expression, phosphorylation or both of different polypeptides.

The methods of this invention for selecting a subject with cancer for treatment, or to not receive treatment, with a molecule targeting HER2, such as, but not limited to treatment with HERCEPTIN®, comprise the step of determining the pattern of expression, phosphorylation or both in a cell or tissue sample from the subject of one or a plurality of polypeptides consisting of: (a) IGFR polypeptide; (b) EGFR polypeptide; (c) NDF polypeptide; (d) phosphorylated S6 ribosomal polypeptide; (e) phosphorylated AKT polypeptide; (f) phosphorylated EKT polypeptide. The combination of polypeptides and pattern of expression, phosphorylation, or both expression and phosphorylation is used to select a subject with cancer for treatment, or to not receive treatment, with a molecule targeting HER2. The methods can include the detection of a pattern of expression, phosphorylation or both of one, two, three, four, five, or all six of these polypeptides. Further, the methods can, but need not, include other steps, including steps such as the detection of a pattern of expression, phosphorylation or both of different polypeptides.

For example, the pattern that identifies a mammalian tumor as responding or that can be used to select a subject with cancer for treatment with a molecule targeted to HER2 is decreased expression of IGFR polypeptide as compared to a non-tumor tissue or cell sample. Alternatively, the detected pattern is normal or increased expression of IGFR polypeptide, accompanied by decreased phosphorylation of AKT polypeptide, decreased phosphorylation of S6 ribosomal polypeptide or both as compared to a non-tumor tissue or cell sample. Another potential detected pattern is normal or increased expression of EGFR polypeptide, accompanied by decreased phosphorylation of ERK polypeptide as compared to a non-tumor tissue or cell sample. Further detected patterns include decreased expression of IGFR polypeptide, accompanied by increased phosphorylation of S6 ribosomal polypeptide as compared to a non-tumor tissue or cell sample. In other embodiments, the detected pattern is decreased expression of IGFR polypeptide, accompanied by increased expression of NDF polypeptide in the mammalian tumor as compared to a non-tumor tissue or cell sample; where further the detected pattern can include increased phosphorylation of S6 ribosomal polypeptide. These identified patterns are understood to be non-limiting.

For example, the pattern that identifies a mammalian tumor as not responding or that can be used to select a subject with cancer to not receive treatment with a molecule targeted to HER2 is normal or increased expression of IGFR polypeptide, accompanied by increased phosphorylation of AKT polypeptide, increased phosphorylation of S6 ribosomal polypeptide, or both as compared to a non-tumor tissue or cell sample. Alternatively, the detected pattern is decreased expression of EGFR polypeptide and increased expression of NDF polypeptide as compared to a non-tumor tissue or cell sample. Or, the detected pattern is decreased expression of EGFR polypeptide as compared to a non-tumor tissue or cell sample. Further, the detected pattern is decreased expression of NDF polypeptide as compared to a non-tumor tissue or cell sample. Or, the detected pattern is decreased expression of EGFR polypeptide and increased phosphorylation of ERK polypeptide as compared to a non-tumor tissue or cell sample. Further, the detected pattern is normal or increased expression of IGFR polypeptide and decreased expression of NDF as compared to a non-tumor tissue or cell sample. These identified patterns are understood to be non-limiting.

In practicing the methods of this invention, staining procedures can be carried out by a person, such as a technician in the laboratory. Alternatively, the staining procedures can be carried out using automated systems. In either case, staining procedures for use according to the methods of this invention are preformed according to standard techniques and protocols well-established in the art.

By "cell or tissue sample" is meant biological samples comprising cells, most preferably tumor cells, that are isolated from body samples, such as, but not limited to, smears, sputum, biopsies, secretions, cerebrospinal fluid, bile, blood, lymph fluid, urine and faeces, or tissue which has been removed from organs, such as breast, lung, intestine, skin, cervix, prostate, and stomach. For example, a tissue samples can comprise a region of functionally related cells or adjacent cells.

The amount of target protein is advantageously quantified by measuring the average optical density of the stained antigens. Concomitantly, the proportion or percentage of total tissue area stained can be readily calculated, for example as the area stained above a control level (such as an antibody threshold level) in the second image. Following visualization of nuclei containing biomarkers, the percentage or amount of such cells in tissue derived from patients after treatment are compared to the percentage or amount of such cells in untreated tissue. For purposes of the invention, "determining" a pattern of expression, phosphorylation, or both expression and phosphorylation of polypeptides is understood broadly to mean merely obtaining the information on such polypeptide(s), either through direct examination or indirectly from, for example, a contract diagnostic service.

Breast cancer tissue sections taken from patients treated with HERCEPTIN® and chemotherapy are analyzed, according to the methods of this invention by immunohistochemistry for expression, phosphorylation, or expression and phosphorylation of erb-B ligands, receptors, downstream signaling proteins or any positive treatment response predictive combination thereof. These measurements can be accomplished, for example, by using tissue microarrays. Tissue microarrays are advantageously used in the methods of the invention, being well-validated method to rapidly screen multiple tissue samples under uniform staining and scoring conditions. (Hoos et al., 2001, *Am J Pathol.* 158: 1245-51). Scoring of the stained arrays can be accomplished by an automated system that accurately quantified the staining observed. The results of this analysis identify biomarkers that best predict patient outcome following treatment, such as HERCEPTIN® therapies. Patient "probability of response" ranging from 0 to 100 percent can be predicted based upon the expression, phosphorylation or both of a small set of ligands, receptors, signaling proteins or predictive combination thereof. Additional samples from breast cancer patients can be analyzed, either as an alternative to or in addition to tissue microarray results. For example, analysis of samples from breast cancer patients can confirm the conclusions from the tissue arrays, if the patient's responses correlate with a specific pattern of receptor expression and/or downstream signaling.

The invention provides, in part, kits for carrying out the methods of the invention. For example, the method provides kits for characterizing a mammalian tumor's responsiveness to a HER2-directed therapy comprising an antibody that binds IGFR polypeptide, and one or more of the following: an antibody that binds phosphorylated AKT polypeptide; an antibody that binds phosphorylated S6 ribosomal polypeptide; an antibody that binds EGFR polypeptide; an antibody that binds HER2 polypeptide; an antibody that binds NDF polypeptide; and an antibody that binds phosphorylated ERK polypeptide. In addition to an antibody that binds IGFR polypeptide, the kit can include one, two, three, four, or all five of the following: an antibody that binds phosphorylated AKT polypeptide; an antibody that binds phosphorylated S6 ribosomal polypeptide; an antibody that binds EGFR polypeptide; an antibody that binds HER2 polypeptide; an antibody that binds NDF polypeptide; and an antibody that binds phosphorylated ERK polypeptide. Further, the kit can include additional components other then the above-identified antibodies, including but not limited to additional antibodies. Such kits may be used, for example, by a clinician or physician as an aid to selecting an appropriate therapy for a particular patient, for example, a breast cancer patient under consideration for HER2-directed therapy.

Particularly useful embodiments of the present invention and the advantages thereof can be understood by referring to Examples 1-5. These Examples are illustrative of specific embodiments of the invention, and various uses thereof. They are set forth for explanatory purposes only, and are not to be taken as limiting the invention.

EXAMPLE 1

Staining Procedure for Biomarkers

Human tumor tissue sections were stained for predictive biomarkers according to the methods of the invention as follows. 10% Neutral Buffered Formalin Paraffin blocks were sectioned at 4 microns and the sections placed onto coated slides. EGFR and HER2 immunostaining was performed by using the pre-diluted EGFR and HER2 antibodies from Ventana Medical Instruments, Inc. (VMSI, Tucson, Ariz.). HER3, Heregulin (NDF), and IGFR antibodies were obtained from NeoMarkers (Fremont, Calif.). TGF-α antibodies were obtained from Oncogene Sciences (San Diego, Calif.). EGFR, HER2/neu, HER3, IGFR, Heregulin, and TGF-α were immunostained using the "BenchMark" (VMSI) with I-VIEW (VMSI) detection chemistry. Antibodies specific for p-ERK (1:100), p-AKT (1:75), and phospho-S6 ribosomal protein were obtained from Cell Signaling Technology (Beverly, Mass.), and immunostained using a labeled streptavidin peroxidase technique. (Vector Elite ABC Kit, Burlingame, Calif.). Prior to staining, slides for p-S6 ribosomal protein, p-ERK and p-AKT were antigen retrieved using 0.1 M citrate buffer, pH 6.0 in the "decloaker" (Biocare Corp.) and the sections incubated overnight with the primary antibodies at 4° C. The next day, the slides were placed onto the Autostainer (Dako Corp.) and the "LSAB2" kit (Dako) was employed as the detection chemistry. DAB (Dako) was used as the chromogen. After immunostaining, all slides were counterstained manually with 4% ethyl green (Sigma).

EXAMPLE 2

Procedure for Western Blot Analysis

Western blot analysis for detecting expression of predictive markers was performed as follows. Cells were lysed in ice-cold buffer (50 mM Tris-HCl (pH 7.5), 137 mM NaCl, 1 mM EDTA, 1% Nonidet P-40, 0.2% Triton X-100, 10% glycerol, 0.1 mM sodium orthovanadate, 10 mM sodium pyrophosphate, 20 mM β-glycerophosphate, 50 mM NaF, 1 mM phenylmethylsulfonyl fluoride, 2 µM leupeptin, and 2 µg/ml aprotinin). Protein concentration was determined with a Bio-Rad Protein Assay Kit (BioRad Laboratories, Hercules, Calif.). Equal amounts of protein, typically 15 µg protein per lane, were separated by gel electrophoresis, for example using pre-cast 4-12% Bis-Tris NuPage gradient gels (Invitrogen) or 7.5% or 4-15% gradient SDS-PAGE under reducing conditions, and transferred to membranes, such as HyBond-C nitrocellulose (Amersham Life Science) or Immobilon-P membranes. Membranes were blocked and then incubated with primary antibodies, for example antibodies against p-AKT and p-ERK (Cell Signaling Technology). Antibody incubation was performed overnight at 4° C. in Tris-buffered saline containing 3% bovine serum albumin/0.1% Tween 20. Signal was detected by chemiluminescence (PerkinElmer Life Sciences), or using a SuperSignal West Femto Maximum sensitivity substrate kit from Pierce (Rockford, Ill.) as described (Xia et al., 2002, *Oncogene* 21: 6255-6263).

EXAMPLE 3

Procedure for Immunohistochemistry

Immunohistochemistry for detecting and measuring predictive biomarker expression, activation or both was performed as follows. HER2/neu, EGFR, HER3, IGFR, TGF-α, Heregulin (NDF), p-ERK, p-AKT, and p-S6 ribosomal protein or phosphorylation levels were quantified using alkaline phosphatase or peroxidase techniques and microscope-based image analysis of immunohistochemically stained slides (as described in Bacus et al., 1997, *Analyt. Quant. Cytol. Histol.* 19: 316-328). Quantification was by means of a CAS 200 image analyzer, as previously described (Bacus & Ruby, 1993, *Pathol Annu,* 28: 179-204). For the purpose of the analysis, tumors were classified as negative or positive for each antibody based upon the level of staining. Statistical analysis was performed using Systat to quantify frequencies and calculate Pearson Chi-squared tests of significance for interactions between variables. In all cases, the p value refers to the significance of the deviation of the distribution of samples from what would be expected based upon the overall population distribution. Comparisons were performed only on samples for which all relevant data were available. As a result, the number of patients included in most comparisons was slightly less then the total number of available samples.

Quantitative immunohistochemistry (IHC) was performed as previously described (Bacus et al., 1997, *Analyt. Quant. Cytol. Histol.* 19: 316-328). EGFR, and erbB-2 (HER2)

immunostaining was performed using pre-diluted EGFR, and erbB-2 (HER2) antibodies from Ventana Medical Systems, Inc. (VMSI, Tucson, Ariz.) on the VMSI automated "Bench-Mark" staining module as described. The VMSI "I-View" detection kit was used for all three of the VMSI pre-diluted primary antibodies according to the manufacturer's instructions. Antibodies to erbB-3 (1:10), Heregulin (1:25), and TGF-α (1:20), were also used for immunostaining using the "BenchMark" with I-VIEW detection chemistry. Antibodies to Phospho-Erk (1:100) and p-AKT (1:75) were used for immunostaining using a labeled streptavidin peroxidase technique as described by the manufacturer. Phospho-Erk and p-AKT slides were antigen retrieved as described by Bacus et al. (1997, *Analyt. Quant. Cytol. Histol.* 19: 316-328). Slides were placed onto the Autostainer (Dako Corp.) and the "LSAB2" kit (Dako) employed as the detection chemistry. After staining, all slides were counterstained manually with 4% ethyl green (Sigma). Investigators preparing and analyzing tissue sections were blinded to both patient tumor type and response to therapy.

For IHC, antibodies to EGFR and erbB-2 were from Ventana Medical Scientific Instruments (VMSI) (Tucson, Ariz.); anti-p-AKT (Ser 437) and p-Erk1/2 were from Cell Signaling Technology Inc. (Beverly, Mass.); antibodies to TGFα, erbB3, heregulin, and IGFR-1 were from NeoMarkers.

EXAMPLE 4

Analysis of Breast Cancer Tissue Microarrays

Tissue microarrays derived from 250 breast cancer patients who received conventional chemotherapy together with HERCEPTIN® were obtained from Clinomics Biosciences (Pittsfield, Mass.). The histology of the tumors varied, with infiltrating ductal carcinoma being the most common. All patients had received post-surgical radiotherapy. The tissue samples in the array were taken before treatment. HER2/neu expression had been determined by using the HercepTest system (DAKO, Carpintera, Calif.) on the original biopsies for all patients. Patient response was based upon the case histories at last follow-up as decided by an independent pathologist provided by Clinomics.

Demographics of these patients are reported in Table 1. The great majority of patients had infiltrating ductal carcinomas and received anthracycline plus cyclophosphamide. Fifty-seven of the patients had metastatic diseases. All patients had received a 4 mg/kg HERCEPTIN® loading dosage and a 2 mg/kg weekly maintenance dosage.

From the original tissue arrays of 250 patients, seventy-five samples were not used in the analysis because of the lack of clinical data or because the sections did not contain usable tumor tissue. Overall, 15% of the remaining patients were disease free or had stable disease after therapy, while 85% relapsed. Of these remaining one hundred and seventy five patients, twenty-eight samples lacked HercepTest results and were therefore also excluded from further analysis. Of the samples for which HercepTest results were obtained, seventy-seven had a HercepTest score of +3, and seventy had +2 or less staining intensity (Table I).

The HercepTest staining scores were confirmed by analyzing HER2/neu expression levels using microarrays (data not shown). HER2/neu expression strongly correlated with patient response; 100% of the 0 or +1 HER2/neu patients relapsed while only 77% of the +3 patients relapsed. This response rate if similar to what has been reported previously (see Baselga, 2002, *Annuals of Oncology* 13: 8-9). Based on these results, further analysis of biomarkers concentrated on patients that expressed HER2 at the highest (+3) level. Of the samples that had the highest HercepTest scores (+3), seventy-four were taken from the primary tumor, two from lymph nodes, and one from an adrenal metastasis.

The seventy-seven patients who overexpressed HER2/neu (+3 HercepTest staining score) were analyzed for expression levels of EGFR, HER3, IGFR, and NDF/Heregulin, and TGF-α, as well as activated downstream signals p-ERK and p-AKT (phosphorylated forms of ERK and AKT) and the downstream signal of mTOR, p-S6 (phosphorylated S6 ribosomal protein). The analysis of receptor kinases reveled that, similar to HER2/neu, EGFR expression also significantly correlated with patient response (Table 2). Among the HERCEPTIN®-treated patients that over-expressed HER-2/neu, 30% of EGFR-positive patients had stable disease or were disease free, while only 9% of EGFR-negative patients did not progress. Among the seventy-seven +3 HER2/neu patients, seventy of them expressed HER3; however, HER3 expression did not significantly correlate with patient response (although the low number of HER3-negative patients limits this comparison in the data set). The growth-factor receptor HER3 is thought to play an important role in downstream erbB signaling because it has a PI3-Kinase docking site and forms active heterodimers with the other erbB receptors. The expression of other growth factor receptors may also mediate patient response, either through direct stimulation or downstream pathways or through transactivation of the erbB receptors.

Expression of erbB ligands, including NDF and TGF-α, also varied among patients (see Table 3). Approximately 70% of the patients expressed high levels of NDF, while approximately 57% expressed high levels of TGF-α. A significant correlation was observed between NDF levels and patient response. A very high proportion of HER2/neu overexpressing patients who were NDF-negative relapsed (91%), whereas only 62% of NDF-positive patients who overexpressed HER2/neu relapsed. In contrast, no predictive relationship was observed between TGF-α levels alone and patient response (see Table 3). The combination of TGF-α or NDF expression and EGFR over-expression, however, did positively correlate with patient response in patients overexpressing HER2/neu ($p=0.02$ and $p=0.03$ respectively) (data not shown).

The activation of heterodimers of HER2 with HER3 or EGFR results in activation of the MAPK and PI3K/AKT pathways. The MAPK pathway was measured by analyzing the level of activation or phosphorylation of ERK (pERK). Analysis and comparison of the levels of activated ERK alone, among patients that overexpressed HER2/neu and who either had stable disease or who relapsed, failed to demonstrate any dramatic effect of elevated pERK levels as a factor for patient response (see Table 4). Similarly, based on this analysis, AKT activation (p-AKT) alone does not appear to be a predictive marker for response among HER2-positive patients treated with HERCEPTIN® (see Table 4). Also, analysis of S6 ribosomal protein phosphorylation, which integrates multiple signals through mTOR and p70 S6 kinase, did not significantly correlate with patient response for patients that overexpressed HER2/neu (see Table 4). If consideration of pERK and pAKT expression is limited to those patients that expressed EGFR and HER2/neu, however, low expression of either of these signaling molecules was a significant predictor of positive response to HERCEPTIN® (Table 5).

To increase the predicative power of the analysis, consideration of two or more of the biomarkers were combined in a multivariate analysis to characterize the tumor. In this analysis, the observation of the combination of HER2/neu and EGFR expression with ERK activation significantly predicted response (see Table 5). For example, patients with low EGFR expression and high ERK phosphorylation failed to respond (0% response), whereas patients with high EGFR expression and low ERK phosphorylation had a high response rate (42% response). Similarly, the combination of high EGFR and HER2/neu with high NDF expression or a combination of high EGFR and HER2/neu with high TGF-α expression predicted a better response compared to patients that had low expression of EGFR and the NDF ligand (data not shown). This comparison was often dramatic. For example, while 39% of the patients with high EGFR, HER2/neu, and NDF expression responded to therapy, none of the patients with high HER2/neu expression but low EGFR and NDF expression responded (data not shown).

The combination of high Her2/neu expression, low IGFR expression, and high S6 ribosomal protein phosphorylation gave high patient response (67%, Table 5). This is in contrast to patients with high HER2/neu and IGFR expression and high S6 ribosomal protein phosphorylation, a high percentage that did not respond to therapy. The best combination of markers for predicting whether patients that overexpressed HER2/neu would respond to HERCEPTIN® therapy were high NDF expression, low IGFR expression, and high S6 phosphorylation (Table 6). In contrast, none of the patients overexpressed HER2/neu and had low NDF expression and high IGFR expression responded to therapy, regardless of S6 status (Table 6). However, these results were obtained using a small sample population of these patients. In patients with high NDF, HER2/neu, and EGFR expression levels, phosphorylation of ERK correlated with a difference in response from 28% (high p-ERK) to 54% (low p-ERK) (Table 6). Similarly, those patients with low levels of p-AKT with any other combination of biomarkers that include the expression of HER2/neu and NDF, did better than those that over-express this protein (results not shown). Taken together, this data shows that HER2/neu together with its ligand and other erbB receptors and ligands, as well as other growth factor receptors play a role in HERCEPTIN® response. Importantly, analysis of a select combination of these proteins correlated with response rates that varied from 0 to 100%.

EXAMPLE 5

Analysis of Breast Cancer Samples

Samples from seven breast cancer patients were obtained from Yale University. The clinical history of these seven patients varied, with some given HERCEPTIN® in combination with chemotherapy as a first line therapy while others were given HERCEPTIN® as an adjuvant therapy. These seven samples were analyzed for receptor, ligand, and signaling protein expression or phosphorylation, and the results compared to the results with the tissue microarray analysis. All seven patients over-expressed HER2/neu, as determined at the time of analysis with the other antibodies immunologically specific for non-HER2/neu polypeptides. The case histories of the patients varied. For example, patient #1 was given HERCEPTIN® plus docetaxel after relapsing with metastatic disease four years after initial presentation. This patient had stable disease for more than a year after commencing combination therapy. Patient #7 was given HERCEPTIN® plus vinorelbine following the discovery of a solitary metastasis seven months after initial radiotherapy. After eight weeks of combination therapy there was progression of disease. Of the seven patients, three showed response to HER-CEPTIN® while the other four failed to respond (Table 7). One of the responders did not express IGFR but did express EGFR and showed positive downstream signaling. The other one of these responders expressed IGFR and EGFR but did not show active downstream signaling in S6 or ERK. All of the non-responders expressed IGFR and had positive S6 phosphorylation. Two of the non-responders also expressed EGFR. These results are consistent with the results obtained from the microarray analysis. Patients with active IGFR receptors as demonstrated by IGFR expression plus S6 phosphorylation are unlikely to respond to HERCEPTIN®, while patients that lack IGFR or have IGFR but no downstream signaling are more likely to respond.

It should be understood that the foregoing disclosure emphasizes certain specific embodiments of the invention and that all modifications or alternatives equivalent thereto are within the spirit and scope of the invention as set forth in the appended claims.

TABLE 1

Demographics

| | number of patients | disease-free or stable disease | relapse |
|---|---|---|---|
| all patients included in study | 175 | 15% | 85% |
| Histology | | | |
| infiltrating ductal carcinoma | 109 | 17% | 83% |
| lobular carcinoma | 7 | 43% | 57% |
| medullary carcinoma | 3 | 33% | 67% |
| metastatic breast carcinoma | 19 | 5% | 95% |
| papillary carcinoma | 3 | 0% | 100% |
| scirrhous carcinoma | 3 | 100% | 0% |
| tubular carcinoma | 3 | 0% | 100% |
| treatment following surgery (followed by Herceptin ®) | | | |
| Doxorubicin | 44 | 2% | 98% |
| anthracycline plus cyclophosphamide | 100 | 23% | 77% |
| Paclitaxel | 3 | 100% | 0% |
| HER2/neu expression tumor | | | |
| 0 or 1 | 17 | 0% | 100% |
| 2 | 53 | 8% | 92% |
| 3 | 77 | 30% | 70% |

Demographics of breast cancer patient samples.

TABLE 2

| patient group | n | % responders | % relapse | P value |
|---|---|---|---|---|
| EGFR positive | 43 | 30% | 70% | 0.002 |
| EGFR negative | 23 | 9% | 91% | |
| HER3 positive | 70 | 29% | 71% | 0.43 |
| HER3 negative | 7 | 43% | 57% | |
| IGFR positive | 33 | 24% | 76% | 0.16 |
| IGFR negative | 35 | 40% | 60% | |

Receptor tyrosine kinase expression versus patient response. Analysis on tissue array samples for which clinical and Herceptest data was available and who over-expressed HER2/neu.

TABLE 3

| patient group | n | % responders | % relapse | P value |
|---|---|---|---|---|
| NDF positive | 55 | 39% | 62% | 0.01 |
| NDF negative | 22 | 9% | 91% | |
| TGF-α positive | 38 | 34% | 66% | 0.56 |
| TGF-α negative | 29 | 28% | 72% | |

Receptor tyrosine kinase ligand expression versus patient response following therapy.

Analysis on tissue array samples for which clinical and Herceptest data was available and who over-expressed HER2/neu.

TABLE 4

| patient group | n | % responders | % relapse | P value |
|---|---|---|---|---|
| p-ERK positive | 36 | 25% | 75% | 0.43 |
| p-ERK negative | 39 | 33% | 67% | |
| p-AKT positive | 24 | 25% | 75% | 0.53 |
| p-AKT negative | 53 | 32% | 68% | |
| p-S6 positive | 27 | 33% | 67% | 0.74 |
| p-S6 negative | 44 | 30% | 70% | |

Downstream protein activation versus patient response following therapy. Analysis on tissue array samples for which clinical and Herceptest data was available and who over-expressed HER2/neu.

TABLE 5

| patient group | n | % responders | % relapse | P value |
|---|---|---|---|---|
| EGFR pos/p-ERK pos | 21 | 14% | 86% | 0.04 |
| EGFR pos/p-ERK neg | 19 | 42% | 58% | |
| EGFR neg/p-ERK pos | 9 | 0% | 100% | |
| EGFR neg/p-ERK neg | 14 | 14% | 86% | |
| EGFR pos/p-AKT pos | 17 | 18% | 82% | 0.07 |
| EGFR pos/p-AKT neg | 26 | 38% | 62% | |
| EGFR neg/p-AKT pos | 5 | 20% | 80% | |
| EGFR neg/p-AKT neg | 18 | 6% | 94% | |
| IGFR pos/p-S6 pos | 13 | 8% | 92% | 0.01 |
| IGFR pos/p-S6 neg | 20 | 35% | 65% | |
| IGFR neg/p-S6 pos | 12 | 67% | 33% | |
| IGFR neg/p-S6 neg | 23 | 26% | 74% | |

Analysis of receptor and downstream protein activation versus response in patients following therapy. Analysis on tissue array samples for which clinical and Herceptest data was available and who over-expressed HER2/neu.

TABLE 6

| patient group | n | % responders | % relapse | P value |
|---|---|---|---|---|
| NDF neg/p-S6 pos/IGFR neg | 2 | 50% | 50% | 0.003 |
| NDF neg/p-S6 neg/IGFR neg | 9 | 11% | 89% | |
| NDF neg/p-S6 neg/IGFR pos | 4 | 0% | 100% | |
| NDF neg/p-S6 pos/IGFR pos | 4 | 0% | 100% | |
| NDF pos/p-S6 pos/IGFR neg | 7 | 100% | 0% | |
| NDF pos/p-S6 pos/IGFR pos | 16 | 44% | 56% | |
| NDF pos/p-S6 neg/IGFR pos | 14 | 36% | 64% | |
| NDF neg/p-ERK pos/EGFR neg | 3 | 0% | 100% | 0.08 |
| NDF neg/p-ERK neg/EGFR neg | 4 | 0% | 100% | |
| NDF neg/p-ERK neg/EGFR pos | 10 | 20% | 80% | |
| NDF neg/p-ERK pos/EGFR pos | 6 | 0% | 100% | |
| NDF pos/p-ERK pos/EGFR neg | 5 | 0% | 100% | |
| NDF pos/p-ERK neg/EGFR pos | 13 | 54% | 46% | |
| NDF pos/p-ERK neg/EGFR neg | 6 | 17% | 83% | |
| NDF pos/p-ERK pos/EGFR pos | 18 | 28% | 72% | |

Analysis of ligand and receptor expression and downstream protein activation versus patient response in patients following therapy. Analysis on tissue array samples for which clinical and Herceptest data was available and who over-expressed HER2/neu.

TABLE 7

| Patient | IGFR | EGFR | p-S6 | p-AKT | p-ERK | Response |
|---|---|---|---|---|---|---|
| #1 | + | + | − | − | − | yes |
| #2 | − | + | + | + | + | yes |
| #3 | + | + | − | + | − | yes |
| #4 | + | − | + | + | + | no |
| #5 | + | + | + | + | − | no |
| #6 | + | − | + | + | − | no |
| #7 | + | + | + | + | + | no |

Receptor tyrosine kinase expression, downstream protein activation and patient response to therapy in seven breast cancer patients. Analysis was of whole tissue sections.

TABLE 8

AKT (NP_005154 GI: 4885061) 480 AMINO ACIDS
(SEQ ID NO: 1)
See, e.g., Staal, S. P., Proc. Natl. Acad. Sci. U.S.A. 84 (14), 5034-5037 (1987).

(SEQ ID NO: 1)
MSDVAIVKEGWLHKRGEYIKTWRPRYFLLKNDGTFIGYKERPQDVDQ
REAPLNNFSVAQCQLMKTERPRPNTFIIRCLQWTTVIERTFHVETPE
EREEWTTAIQTVADGLKKQEEEEMDFRSGSPSDNSGAEEMEVSLAKP
KHRVTMNEFEYLKLLGKGTFGKVILVKEKATGRYYAMKILKKEVIVA
KDEVAHTLTENRVLQNSRHPFLTALKYSFQTHDRLCFVMEYANGGEL
FFHLSRERVFSEDRARFYGAEIVSALDYLHSEKNVVYRDLKLENLML
DKDGHIKITDFGLCKEGIKDGATMKTFCGTPEYLAPEVLEDNDYGRA
VDWWGLGVVMYEMMCGRLPFYNQDHEKLFELILMEEIRFPRTLGPEA
KSLLSGLLKKDPKQRLGGGSEDAKEIMQHRFFAGIVWQHVYEKKLSP
PFKPQVTSETDTRYFDEEFTAQMITITPPDQDDSMECVDSERRPHFP
QFSYSASSTA

S6 (NP_001001, GI: 17158044) 249 AMINO ACIDS
(SEQ ID NO: 2)
See, e.g., Pata et al., (1992) Gene 121 (2), 387-392.

(SEQ ID NO: 2)
MKLNISFPATGCQKLIEVDDERKLRTFYEKRMATEVAADALGEEWKG
YVVRISGGNDKQGFPMKQGVLTHGRVRLLLSKGHSCYRPRRTGERKR
KSVRGCIVDANLSVLNLVIVKKGEKDIPGLTDTTVPRRLGPKRASRI
RKLFNLSKEDDVRQYVVRKPLNKEGKKPRTKAPKIQRLVTPRVLQHK
RRRIALKKQRTKKNKEEAAEYAKLLAKRMKEAKEKRQEQIAKRRRLS
SLRASTSKSESSQK

ERK (XP_055766, GI: 20562757) 379 AMINO ACIDS
(SEQ ID NO: 3)
See, e.g., Butch et al., J Biol Chem., 1996., 271(8): 4230-5.

(SEQ ID NO: 3)
MAAAAAQGGGGGEPRRTEGVGPGVPGEVEMVKGQPFDVGPRYTQLQY
IGEGAYGMVSSAYDHVRKTRVAIKKISPFEHQTYCQRTLREIQILLR
FRHENVIGIRDILRASTLEAMRDVYIVQDLMETDLYKLLKSQQLSND
HICYFLYQILRGLKYIHSANVLHRDLKPSNLLINTTCDLKICDFGLA
RIADPEHDHTGFLTEYVATRWYRAPEIMLNSKGYTKSIDIWSVGCIL
AEMLSNRPIFPGKHYLDQLNHILGILGSPSQEDLNCIINMKARNYLQ
SLPSKTKVAWAKLFPKSDSKALDLLDRMLTFNPNKRITVEEALAHPY
LEQYYDPTDEPVAEEPFTFAMELDDLPKERLKELIFQETARFQPGVL
EAP

The invention claimed is:

1. A method for identifying a breast tumor likely to respond to trastuzumab, comprising:
   measuring by immunohistochemistry in a tissue sample obtained from the breast tumor:
   a) expression of epidermal growth factor receptor (EGFR) polypeptide; and
   b) phosphorylation of extracellular signal-regulated kinase (ERK) polypeptide, wherein phosphorylation of ERK polypeptide is measured using an antibody specific for an epitope comprising a phosphorylated threonine at position 202 of SEQ ID NO: 3, a phosphorylated tyrosine at position 204 of SEQ ID NO: 3, or a combination thereof; and
   identifying the breast tumor as a breast tumor likely to respond to trastuzumab, if the breast tumor is positive for EGFR polypeptide expression and negative for phosphorylation of ERK polypeptide.

2. The method of claim 1, wherein the sample is a biopsy sample.

3. The method of claim 2, wherein the biopsy sample is a paraffin-embedded sample.

4. The method of claim 1, further comprising identifying the breast tumor as not likely to respond to trastuzumab if the breast tumor is negative for EGFR polypeptide expression and positive for phosphorylation of ERK polypeptide.

5. A method for selecting a subject with a breast tumor for treatment with trastuzumab, comprising:
   measuring by immunohistochemistry in a tissue sample obtained from the breast tumor:
   a) expression of epidermal growth factor receptor (EGFR) polypeptide; and
   b) phosphorylation of extracellular signal-regulated kinase (ERK) polypeptide, wherein phosphorylation of ERK polypeptide is measured using an antibody specific for an epitope comprising a phosphorylated threonine at position 202 of SEQ ID NO: 3, a phosphorylated tyrosine at position 204 of SEQ ID NO: 3, or a combination thereof;
   identifying the breast tumor as a breast tumor likely to respond to trastuzumab if the breast tumor is positive for EGFR polypeptide expression and negative for phosphorylation of ERK polypeptide; and
   selecting a subject with a breast tumor identified as likely to respond to trastuzumab for treatment with trastuzumab.

6. The method of claim 5, wherein the sample is a biopsy sample.

7. The method of claim 6, wherein the biopsy sample is a paraffin-embedded sample.

8. The method of claim 5, wherein the breast tumor has previously been treated with at least one chemotherapeutic.

9. The method of claim 8, wherein the chemotherapeutic comprises cisplatin, doxorubicin, or taxol.

10. The method of claim 5, further comprising not selecting the subject for treatment with trastuzumab if the breast tumor is negative for EGFR polypeptide expression and positive for phosphorylation of ERK polypeptide.

11. The method of claim 5, further comprising administering trastuzumab to the selected subject.

12. A method for identifying a breast tumor likely to respond to trastuzumab, comprising:
   measuring in a sample obtained from the breast tumor:
   a) expression of epidermal growth factor receptor (EGFR) polypeptide; and
   b) phosphorylation of extracellular signal-regulated kinase (ERK) polypeptide, wherein phosphorylation of ERK polypeptide is measured using an antibody specific for an epitope comprising a phosphorylated threonine at position 202 of SEQ ID NO: 3, a phosphorylated tyrosine at position 204 of SEQ ID NO: 3, or a combination thereof;
   identifying the breast tumor as a breast tumor likely to respond to trastuzumab, if the breast tumor is positive for EGFR polypeptide expression and negative for phosphorylation of ERK polypeptide; and
   administering trastuzumab to the subject from which the breast tumor sample was obtained if the breast tumor is positive for EGFR polypeptide expression and negative for phosphorylation of ERK polypeptide.

* * * * *

SEQUENCE LISTING

<160> NUMBER OF SEQ ID NOS: 3

<210> SEQ ID NO 1
<211> LENGTH: 480
<212> TYPE: PRT
<213> ORGANISM: Homo sapiens

<400> SEQUENCE: 1

```
Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365
```

```
Pro Arg Thr Leu Gly Pro Glu Ala Lys Ser Leu Leu Ser Gly Leu Leu
    370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
                435                 440                 445

Ile Thr Pro Pro Asp Gln Asp Asp Ser Met Glu Cys Val Asp Ser Glu
        450                 455                 460

Arg Arg Pro His Phe Pro Gln Phe Ser Tyr Ser Ala Ser Ser Thr Ala
465                 470                 475                 480

<210> SEQ ID NO 2
<211> LENGTH: 249
<212> TYPE: PRT
<213> ORGANISM: Homo sapiens

<400> SEQUENCE: 2

Met Lys Leu Asn Ile Ser Phe Pro Ala Thr Gly Cys Gln Lys Leu Ile
1               5                   10                  15

Glu Val Asp Asp Glu Arg Lys Leu Arg Thr Phe Tyr Glu Lys Arg Met
            20                  25                  30

Ala Thr Glu Val Ala Ala Asp Ala Leu Gly Glu Glu Trp Lys Gly Tyr
        35                  40                  45

Val Val Arg Ile Ser Gly Gly Asn Asp Lys Gln Gly Phe Pro Met Lys
    50                  55                  60

Gln Gly Val Leu Thr His Gly Arg Val Arg Leu Leu Leu Ser Lys Gly
65                  70                  75                  80

His Ser Cys Tyr Arg Pro Arg Arg Thr Gly Glu Arg Lys Arg Lys Ser
                85                  90                  95

Val Arg Gly Cys Ile Val Asp Ala Asn Leu Ser Val Leu Asn Leu Val
            100                 105                 110

Ile Val Lys Lys Gly Glu Lys Asp Ile Pro Gly Leu Thr Asp Thr Thr
        115                 120                 125

Val Pro Arg Arg Leu Gly Pro Lys Arg Ala Ser Arg Ile Arg Lys Leu
    130                 135                 140

Phe Asn Leu Ser Lys Glu Asp Asp Val Arg Gln Tyr Val Val Arg Lys
145                 150                 155                 160

Pro Leu Asn Lys Glu Gly Lys Lys Pro Arg Thr Lys Ala Pro Lys Ile
                165                 170                 175

Gln Arg Leu Val Thr Pro Arg Val Leu Gln His Lys Arg Arg Arg Ile
            180                 185                 190

Ala Leu Lys Lys Gln Arg Thr Lys Lys Asn Lys Glu Glu Ala Ala Glu
        195                 200                 205

Tyr Ala Lys Leu Leu Ala Lys Arg Met Lys Glu Ala Lys Glu Lys Arg
    210                 215                 220

Gln Glu Gln Ile Ala Lys Arg Arg Arg Leu Ser Ser Leu Arg Ala Ser
225                 230                 235                 240

Thr Ser Lys Ser Glu Ser Ser Gln Lys
                245

<210> SEQ ID NO 3
```

```
<211> LENGTH: 379
<212> TYPE: PRT
<213> ORGANISM: Homo sapiens

<400> SEQUENCE: 3
```

| | | | | | | | | | | | | | | |
|---|---|---|---|---|---|---|---|---|---|---|---|---|---|---|
| Met | Ala | Ala | Ala | Ala | Gln | Gly | Gly | Gly | Gly | Glu | Pro | Arg | Arg | |
| 1 | | | | 5 | | | | | 10 | | | | 15 | |
| Thr | Glu | Gly | Val | Gly | Pro | Gly | Val | Pro | Gly | Glu | Val | Glu | Met | Val | Lys |
| | | | 20 | | | | | 25 | | | | | 30 | | |
| Gly | Gln | Pro | Phe | Asp | Val | Gly | Pro | Arg | Tyr | Thr | Gln | Leu | Gln | Tyr | Ile |
| | | 35 | | | | | 40 | | | | | 45 | | | |
| Gly | Glu | Gly | Ala | Tyr | Gly | Met | Val | Ser | Ser | Ala | Tyr | Asp | His | Val | Arg |
| | 50 | | | | | 55 | | | | | 60 | | | | |
| Lys | Thr | Arg | Val | Ala | Ile | Lys | Lys | Ile | Ser | Pro | Phe | Glu | His | Gln | Thr |
| 65 | | | | | 70 | | | | | 75 | | | | | 80 |
| Tyr | Cys | Gln | Arg | Thr | Leu | Arg | Glu | Ile | Gln | Ile | Leu | Leu | Arg | Phe | Arg |
| | | | | 85 | | | | | 90 | | | | | 95 | |
| His | Glu | Asn | Val | Ile | Gly | Ile | Arg | Asp | Ile | Leu | Arg | Ala | Ser | Thr | Leu |
| | | | 100 | | | | | 105 | | | | | 110 | | |
| Glu | Ala | Met | Arg | Asp | Val | Tyr | Ile | Val | Gln | Asp | Leu | Met | Glu | Thr | Asp |
| | | 115 | | | | | 120 | | | | | 125 | | | |
| Leu | Tyr | Lys | Leu | Leu | Lys | Ser | Gln | Gln | Leu | Ser | Asn | Asp | His | Ile | Cys |
| | 130 | | | | | 135 | | | | | 140 | | | | |
| Tyr | Phe | Leu | Tyr | Gln | Ile | Leu | Arg | Gly | Leu | Lys | Tyr | Ile | His | Ser | Ala |
| 145 | | | | | 150 | | | | | 155 | | | | | 160 |
| Asn | Val | Leu | His | Arg | Asp | Leu | Lys | Pro | Ser | Asn | Leu | Leu | Ile | Asn | Thr |
| | | | | 165 | | | | | 170 | | | | | 175 | |
| Thr | Cys | Asp | Leu | Lys | Ile | Cys | Asp | Phe | Gly | Leu | Ala | Arg | Ile | Ala | Asp |
| | | | 180 | | | | | 185 | | | | | 190 | | |
| Pro | Glu | His | Asp | His | Thr | Gly | Phe | Leu | Thr | Glu | Tyr | Val | Ala | Thr | Arg |
| | | 195 | | | | | 200 | | | | | 205 | | | |
| Trp | Tyr | Arg | Ala | Pro | Glu | Ile | Met | Leu | Asn | Ser | Lys | Gly | Tyr | Thr | Lys |
| | 210 | | | | | 215 | | | | | 220 | | | | |
| Ser | Ile | Asp | Ile | Trp | Ser | Val | Gly | Cys | Ile | Leu | Ala | Glu | Met | Leu | Ser |
| 225 | | | | | 230 | | | | | 235 | | | | | 240 |
| Asn | Arg | Pro | Ile | Phe | Pro | Gly | Lys | His | Tyr | Leu | Asp | Gln | Leu | Asn | His |
| | | | | 245 | | | | | 250 | | | | | 255 | |
| Ile | Leu | Gly | Ile | Leu | Gly | Ser | Pro | Ser | Gln | Glu | Asp | Leu | Asn | Cys | Ile |
| | | | 260 | | | | | 265 | | | | | 270 | | |
| Ile | Asn | Met | Lys | Ala | Arg | Asn | Tyr | Leu | Gln | Ser | Leu | Pro | Ser | Lys | Thr |
| | | 275 | | | | | 280 | | | | | 285 | | | |
| Lys | Val | Ala | Trp | Ala | Lys | Leu | Phe | Pro | Lys | Ser | Asp | Ser | Lys | Ala | Leu |
| | 290 | | | | | 295 | | | | | 300 | | | | |
| Asp | Leu | Leu | Asp | Arg | Met | Leu | Thr | Phe | Asn | Pro | Asn | Lys | Arg | Ile | Thr |
| 305 | | | | | 310 | | | | | 315 | | | | | 320 |
| Val | Glu | Glu | Ala | Leu | Ala | His | Pro | Tyr | Leu | Glu | Gln | Tyr | Tyr | Asp | Pro |
| | | | | 325 | | | | | 330 | | | | | 335 | |
| Thr | Asp | Glu | Pro | Val | Ala | Glu | Pro | Phe | Thr | Phe | Ala | Met | Glu | Leu |
| | | | 340 | | | | | 345 | | | | | 350 | | |
| Asp | Asp | Leu | Pro | Lys | Glu | Arg | Leu | Lys | Glu | Leu | Ile | Phe | Gln | Glu | Thr |
| | | 355 | | | | | 360 | | | | | 365 | | | |
| Ala | Arg | Phe | Gln | Pro | Gly | Val | Leu | Glu | Ala | Pro | | | | | |
| | 370 | | | | | 375 | | | | | | | | | |